United States Patent
Dörr et al.

(10) Patent No.: US 9,458,300 B2
(45) Date of Patent: Oct. 4, 2016

(54) HYDROPHILIC, ALIPHATIC POLYURETHANE FOAMS

(75) Inventors: Sebastian Dörr, Düsseldorf (DE); Meike Niesten, Köln (DE)

(73) Assignee: Covestro Deutschland AG, Leverkusen (DE)

( * ) Notice: Subject to any disclaimer, the term of this patent is extended or adjusted under 35 U.S.C. 154(b) by 352 days.

(21) Appl. No.: 13/881,390

(22) PCT Filed: Oct. 25, 2011

(86) PCT No.: PCT/EP2011/068588
§ 371 (c)(1),
(2), (4) Date: Jun. 19, 2013

(87) PCT Pub. No.: WO2012/055834
PCT Pub. Date: May 3, 2012

(65) Prior Publication Data
US 2013/0261200 A1    Oct. 3, 2013

(30) Foreign Application Priority Data

Oct. 27, 2010 (EP) .................................. 10189041

(51) Int. Cl.
| | | |
|---|---|---|
| *C08G 18/10* | (2006.01) | |
| *C08J 9/00* | (2006.01) | |
| *A61L 15/16* | (2006.01) | |
| *A61L 15/42* | (2006.01) | |
| *C08G 18/28* | (2006.01) | |
| *A61L 15/26* | (2006.01) | |
| *C08G 101/00* | (2006.01) | |

(52) U.S. Cl.
CPC .............. *C08J 9/0066* (2013.01); *A61L 15/16* (2013.01); *A61L 15/26* (2013.01); *A61L 15/425* (2013.01); *C08G 18/10* (2013.01); *C08G 18/283* (2013.01); *C08G 2101/0083* (2013.01)

(58) Field of Classification Search
CPC ...... C08J 9/0066; A61L 15/16; A61L 15/26; A61L 15/425; C08G 18/10; C08G 18/283; C08G 18/302; C08G 18/8064; C08G 18/792; C08G 2101/0083; C08L 75/04
See application file for complete search history.

(56) References Cited

U.S. PATENT DOCUMENTS

| | | | |
|---|---|---|---|
| 3,903,232 A | 9/1975 | Wood et al. | |
| 4,137,200 A * | 1/1979 | Wood et al. | ................... 521/159 |
| 4,299,924 A * | 11/1981 | Nomura et al. | ............... 521/131 |
| 5,064,653 A | 11/1991 | Sessions et al. | |
| 5,065,752 A | 11/1991 | Sessions et al. | |
| 5,296,518 A | 3/1994 | Grasel et al. | |
| 6,051,622 A * | 4/2000 | Kinkelaar et al. | ............. 521/159 |
| 6,191,179 B1 | 2/2001 | Scherzer et al. | |
| 2009/0148395 A1 | 6/2009 | Fugmann et al. | |
| 2011/0184080 A1 | 7/2011 | Schonberger et al. | |

FOREIGN PATENT DOCUMENTS

| | | |
|---|---|---|
| DE | 102007048080 A1 | 4/2009 |
| EP | 0482467 A2 | 4/1992 |
| EP | 949285 A1 | 10/1999 |
| EP | 10000158.5 | 12/2009 |
| EP | 2143744 A1 | 1/2010 |
| EP | 09075400.6 | 2/2010 |
| EP | 2336211 A1 | 6/2011 |
| GB | 1571730 A | 7/1980 |
| WO | WO-02/074826 A1 | 9/2002 |
| WO | WO-03/097727 A1 | 11/2003 |
| WO | WO-2004013215 A1 | 2/2004 |
| WO | WO-2010003559 A1 | 1/2010 |

OTHER PUBLICATIONS

International Search Report for PCT/EP2011/068588 mailed Jan. 24, 2012.

* cited by examiner

*Primary Examiner* — John Cooney
(74) *Attorney, Agent, or Firm* — Drinker Biddle & Reath LLP

(57) ABSTRACT

The invention relates to a method for producing hydrophilic, aliphatic polyurethane foams. The invention further relates to special compositions for producing polyurethane foams either using the method according to the invention or using the polyurethane foams obtained from the compositions according to the invention, and to the use of the polyurethane foams as a wound dressing, cosmetic item, or incontinence product.

18 Claims, 1 Drawing Sheet

HYDROPHILIC, ALIPHATIC POLYURETHANE FOAMS

RELATED APPLICATIONS

This application is a national stage application (under 35 U.S.C. §371) of PCT/EP2011/068588, filed Oct. 25, 2011, which claims benefit of European application 10189041.6, filed Oct. 27, 2010, both of which are incorporated by reference herein.

The invention relates to a process for producing hydrophilic aliphatic polyurethane foams. The invention further relates to specific compositions for producing the polyurethane foams by the process of the invention, to polyurethane foams obtainable from the compositions of the invention, and also to using the polyurethane foams as a primary wound dressing, as a cosmetic article or as an incontinence product.

Processes for producing hydrophilic aliphatic polyurethane foams and the use of foams of this type as primary wound dressings are disclosed in the prior art. EP 949 285 A describes the reaction of polyisocyanates with primary diamines, low molecular weight polyols and high molecular weight polyols to form foams of this type. However, appreciable portions of the isocyanate-reactive substances may not become converted in this reaction and are then extractable from the hydrophilic foam.

GB 1571730 describes the reaction of high vapor pressure diisocyanates such as isophorone diisocyanate (IPDI) and bis(isocyanatocyclohexyl)methane (HMDI) with polyols to give polyurethane foams. Again, unconverted components are left behind. Moreover, using free, non-derivatized diisocyanates is problematic from an occupational hygiene viewpoint. WO 2004013215 likewise utilizes volatile diisocyanates.

WO 2003/097727, U.S. Pat. No. 5,065,752 and U.S. Pat. No. 5,064,653 describe foam-forming reactions of prepolymers in the presence of acrylamide-acrylic acid copolymers. These products are not chemically attached and are completely extractable, which is not desirable.

In U.S. Pat. No. 3,903,232, prepolymers are reacted with polyethers. Again, there is a risk of unattached polyols being produced with the foams produced here. U.S. Pat. No. 5,296,518 similarly describes the reaction of prepolymers with polyethers wherein three different polyols are used, which calls the economics of this process into question. Furthermore, the process described therein is incapable of making certain that there are no low molecular weight isocyanates left in the mixture.

PCT application WO 2010/003559 and the as yet unpublished European patent applications numbered 10000158.5 and 09015400.6 describe processes for producing particularly hydrophilic polyurethane foams. These foams are based on aliphatic isocyanates. Compared with the known processes for producing polyurethane foams by using aromatic isocyanates, the processes described here have longer reaction times due to the lower reactivity of the aliphatic isocyanates used. However, to be able to process the systems on existing equipment, designed for fast-reacting aromatic prepolymers, the reaction times of the processes described need to be reduced without this adversely affecting the foam properties.

The present invention therefore has for its object to provide a process for producing hydrophilic aliphatic polyurethane foams having a reduced reaction time compared with the processes known in the prior art.

The polyurethane foams obtainable by the process of the present invention shall more particularly be usable as a constituent of a primary wound dressing, as a constituent of a cosmetic article or as a constituent of an incontinence product and therefore shall contain but little by way of extractable constituents. Moreover, only polyisocyanates having a low vapor pressure, i.e., no unmodified diisocyanates, should be used to produce these foams. The hydrophilic aliphatic polyurethane foams should also have fast and deep absorbance in respect of physiological saline and/or wound fluid. Lastly, primary wound dressings comprising the polyurethane foams shall also be cell-compatible, i.e., noncytotoxic, and optimally conform to the shape of the wound in use.

This object is achieved according to the invention by a process for producing hydrophilic aliphatic polyurethane foams, which comprises compositions comprising
  A) isocyanate-functional prepolymers obtainable by reaction of
    A1) low molecular weight aliphatic diisocyanates having a molar mass of 140 to 278 g/mol with
    A2) di- to hexafunctional polyalkylene oxides having an OH number of 22.5 to 112 mg KOH/g and an ethylene oxide content of 50 to 100 mol %, based on the total amount of oxyalkylene groups present,
  B) alkali metal salts of weak inorganic acids,
  C) water,
  D) optionally heterocyclic 4-ring or 6-ring oligomers of low molecular weight aliphatic diisocyanates having a molar mass of 140 to 278 g/mol,
  E) optionally catalysts,
  F) optionally surfactants,
  G) optionally mono- or polyhydric alcohols, and
  H) optionally hydrophilic polyisocyanates obtainable by reaction of
    H1) low molecular weight aliphatic diisocyanates having a molar mass of 140 to 278 g/ml and/or polyisocyanates obtainable therefrom with an isocyanate functionality of 2 to 6, with
    H2) monofunctional polyalkylene oxides having an OH number of 10 to 250 and an ethylene oxide content of 50 to 100 mol %, based on the total amount of oxyalkylene groups present,
  being provided, foamed and cured, wherein alkali metal salts of weak inorganic acids B) are used whose corresponding free acids have a $pK_a$ value of ≥4.0 in water at 25° C.

The process of the present invention needs less reaction time to produce aliphatic polyurethane foams than the processes cited above, which are described in the prior art. That is, the individual components are quicker to undergo complete conversion here, so the process of the present invention can also be practiced on existing equipment designed for producing foams from fast-reacting aromatic prepolymers. Moreover, despite the accelerated reaction, there is sufficient pot life, i.e., the reaction between the components is not too quick for complete mixing to take place.

Surprisingly, adding organic acids or salts thereof, for instance the sodium oleate mentioned in WO 2010/003559, does not provide any suitable acceleration in the reaction even on distinctly raising the concentration in the composition.

In addition, the polyurethane foams obtainable by the process of the present invention have comparable positive chemical and physical properties to the foams known from WO 2010/003559. Thus, their absorbance of physiological saline or wound fluid is high. They also have but a small fraction of extractable constituents and hence are very highly cell-compatible.

The absorbance of physiological saline on the part of the polyurethane foams obtained by the process according to the present invention is typically in the range from 400 to 2000% (mass of absorbed fluid, divided by mass of dry foam; determination to DIN EN 13726-1, Part 3.2). Compared with other hydrophilic foams, therefore, the polyurethane foams can be used to achieve a very high absorption of physiological saline even without the use of superabsorbent polymers. It will be appreciated, however, that incorporation of superabsorbents is also possible with the polyurethane foams obtained by the process according to the present invention, although this is not preferable with these foams, since their absorption is already very high.

Figure 1:
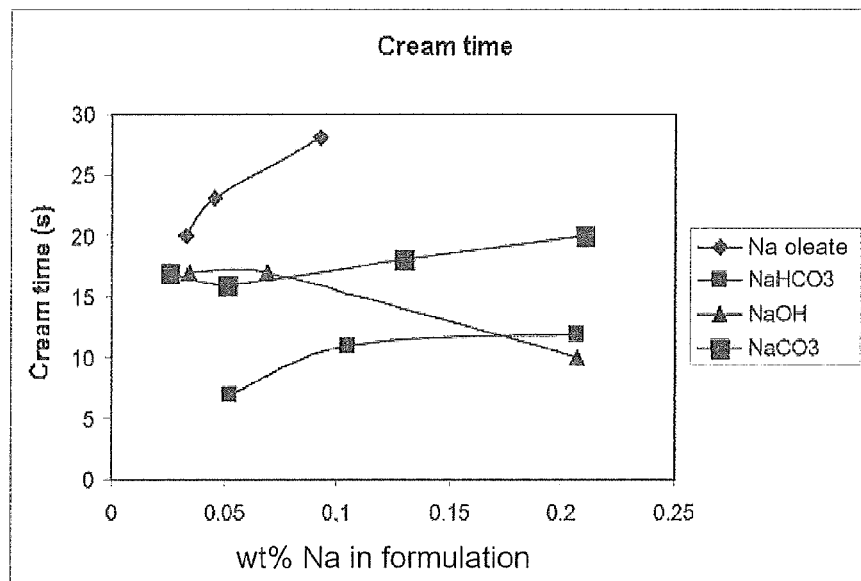
FIG. 1 shows cream time for alkali metal salts as function of sodium concentration in the formulation.

The polyurethane foams obtained by the process according to the present invention further have pleasant haptics and a porous, at least partly open-celled structure comprising intercommunicating cells. The apparent density of these polyurethane foams is typically in the range from 0.01 to 0.5 g/cm$^3$ (determination to DIN 53420). The polyurethane foams further have good mechanical strength and high elasticity. Typically, tensile strength is greater than 30 kPa and elongation at break is greater than 20% (determination to DIN 53504, DIN 53455).

In one further development of the invention, isocyanate-functional prepolymers A) having a weight fraction of below 1.0 wt %, preferably of below 0.5 wt %, for low molecular weight aliphatic diisocyanates having a molar mass of 140 to 278 g/mol, based on the prepolymer, are used. This content can be achieved through appropriately chosen use quantities of diisocyanates A1) and polyalkylene oxides A2). However, it is preferable for diisocyanate A1) to be used in excess in the subsequent separation, preferably by distillation, of unreacted diisocyanates. The polyurethane foams obtainable in this embodiment have a particularly low level of potentially harmful extractable constituents and hence are particularly highly cell-compatible.

The isocyanate-functional prepolymers A) are typically prepared by reacting 1 mol equivalent of polyalkylene oxides A2) with 1 to 20 mol, preferably 1 to 10 mol and more preferably 5 to 10 mol of diisocyanate A1). The reaction is typically carried out at 25 to 140° C., preferably 60 to 100° C. When excess diisocyanate was used, the subsequent removal of the excess is preferably effected by thin-film distillation.

Before, during and after the reaction or distillative removal of the excess diisocyanate, acidic or alkylating stabilizers, such as benzoyl chloride, isophthaloyl chloride, methyl tosylate, chloropropionic acid, HCl or antioxidants, such as di-tert-butylcresol or tocopherol can be added.

The isocyanate group content (determined by DIN EN ISO 11909) of the isocyanate-functional prepolymers A) is preferably in the range from 1.5 to 4.5 wt %, more preferably in the range from 1.5 to 3.5 wt % and even more preferably in the range from 1.5 to 3.0 wt %.

Examples of suitable low molecular weight aliphatic diisocyanates A1) are hexamethylene diisocyanate (HDI), isophorone diisocyanate (IPDI), butylene diisocyanate (BDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, of which hexamethylene diisocyanate, isophorone diisocyanate, butylene diisocyanate and bis(isocyanatocyclohexyl)methane are preferred.

In a particularly preferred embodiment of the invention exclusively hexamethylene diisocyanate (HDI), isophorone diisocyanate (IPDI) or mixtures thereof are used as low molecular weight aliphatic diisocyanates A1).

Polyalkylene oxides A2) are preferably copolymers of ethylene oxide and propylene oxide having an ethylene oxide content, based on the total amount of oxyalkylene groups present, of 50 to 100 mol %, preferably 60 to 85 mol %, and started on polyols or amines. Suitable starters of this kind are glycerol, trimethylolpropane (TMP), sorbitol, pentaerythritol, triethanolamine, ammonia or ethylenediamine.

The number-average molecular weight of the polyalkylene oxides A2) is typically in the range from 1000 to 15 000 g/mol and preferably in the range from 3000 to 8500 g/mol.

The polyalkylene oxides A2) can further have OH functionalities of 2 to 6, preferably of 3 to 6 and more preferably of 3 to 4.

In a further preferred embodiment of the invention, alkali metal salts of weak inorganic acids B) are used whose corresponding free acids have a $pK_a$ value of $\geq 4.0$ and $\leq 14.0$ in water at 25° C.

Potassium hydroxide, sodium hydroxide, potassium carbonate, sodium carbonate and sodium bicarbonate are examples of particularly suitable alkali metal salts of weak inorganic acids B), while any desired mixtures of these salts shall also be encompassed.

It is particularly preferable when the alkali metal salts of weak inorganic acids B) are selected from the group sodium hydroxide, sodium bicarbonate and sodium carbonate. A particularly short reaction time results in this case.

The water used C) can be used as such, as water of crystallization of a salt, as solution in a dipolar aprotic solvent or else as an emulsion. Preferably, the water is used as such or in a dipolar aprotic solvent. It is very particularly preferred to use water as such.

Optionally used ring oligomers D) are heterocyclic 4-ring or 6-ring oligomers of low molecular weight aliphatic diisocyanates having a molar mass of 140 to 278 g/mol such as isocyanurates, iminooxadiazinediones or uretidiones of the aforementioned low molecular weight aliphatic diisocyanates. Heterocyclic 4-ring oligomers such as uretidiones are preferred. The increased isocyanate group content due to the use of ring oligomers D) provides better foaming due to more $CO_2$ being formed in the isocyanate-water reaction.

To further accelerate the reaction, catalysts E) may be added. The catalysts in question are typically compounds with which a person skilled in the art is familiar from polyurethane technology. Preference here is given to compounds from the group consisting of catalytically active metal salts, amines, amidines and guanidines. Specific examples are dibutyltin dilaurate (DBTL), tin octoate (SO), tin acetate, zinc octoate (ZO), 1,8-diazabicyclo[5.4.0]undec-7-ene (DBU), 1,5-diazabicyclo[4.3.0]non-5-ene (DBN), 1,4-diazabicyclo[3.3.0]oct-4-ene (DBO), N-ethylmorpholine (NEM), triethylenediamine (DABCO), pentamethylguanidine (PMG), tetramethylguanidine (TMG), cyclotetramethylguanidine (TMGC), n-decyltetramethylguanidine (TMGD), n-dodecyltetramethylguanidine (TMGDO), dimethylaminoethyltetramethylguanidine (TMGN), 1,1,4,4,5,5- hexamethylisobiguanidine (HMIB), phenyltetramethylguanidine (TMGP) and hexamethyleneoctamethylbiguanidine (HOBG).

However, it is particularly preferable for no catalysts E) to be used.

Surfactants F) can be added to improve foam formation, foam stability or the properties of the resulting polyurethane foam, in which case such additives can in principle be any known anionic, cationic, amphoteric and nonionic surfactants and also mixtures thereof. Preference is given to using alkylpolyglycosides, EO-PO block copolymers, alkyl or aryl alkoxylates, siloxane alkoxylates, esters of sulfosuccinic acid and/or alkali or alkaline earth metal alkanoates. Particular preference is given to using EO-PO block copolymers, and very particularly preferably the EO-PO block copolymers are solely used as surfactants F).

In addition, mono- and polyhydric alcohols G) and mixtures thereof can be used to improve the properties of the resulting polyurethane foam. Examples of these alcohols are mono- or polyhydric alcohols or polyols, such as ethanol, propanol, butanol, decanol, tridecanol, hexadecanol, ethylene glycol, neopentyl glycol, butanediol, hexanediol, decanediol, trimethylolpropane, glycerol, pentaerythritol, monofunctional polyether alcohols and polyester alcohols, polyether diols and polyester diols.

It is likewise optional to include hydrophilic polyisocyanates H) among the reactants. The hydrophilic polyisocyanates H) are typically prepared by adjusting the ratio of monofunctional polyalkylene oxides H2) to low molecular weight aliphatic diisocyanates H1) such that for every 1 mol of OH groups of the monofunctional polyalkylene oxides there are from 1.25 to 15 mol, preferably from 2 to 10 mol and more preferably from 2 to 6 mol of NCO groups of low molecular weight aliphatic diisocyanate H1). This is followed by the allophanatization/biuretization and/or isocyanurate formation/uretidione formation. When the polyalkylene oxides H2) become bonded to the aliphatic diisocyanates H1) via urethane groups, it is preferably an allophanatization which takes place subsequently. It is further preferable for isocyanurate structural units to be formed.

An alternative way to prepare the hydrophilic polyisocyanates H) typically involves reacting 1 mol of OH groups of the monofunctional polyalkylene oxide component H2) with 1.25 to 15 mol, preferably with 2 to 10 mol and more preferably 2 to 6 mol of NCO groups of a polyisocyanate H1) having an isocyanate functionality of 2 to 6, based on aliphatic diisocyanates. Exemplary of such polyisocyanates H1) are biuret structures, isocyanurates/uretidiones based on aliphatic diisocyanates. The polyisocyanates H1) and the polyalkylene oxides H2) are preferably linked together via a urethane group or a urea group, although particularly the linking via urethane groups is preferable.

The reaction can be carried out in the presence of urethanization catalysts such as tin compounds, zinc compounds, amines, guanidines or amidines, or in the presence of allophanatization catalysts such as zinc compounds.

The reaction temperature is typically in the range from 25 to 140° C. and preferably in the range from 60 to 100° C.

When excess low molecular weight diisocyanate was used, excess low molecular weight aliphatic diisocyanate is subsequently removed, preferably by thin film distillation.

Before, during and after the reaction or distillative removal of excess diisocyanate, acidic or alkylating stabilizers, such as benzoyl chloride, isophthaloyl chloride, methyl tosylate, chloropropionic acid, HCl or antioxidants, such as di-tert-butylcresol or tocopherol can be added.

The NCO content (determined to DIN EN ISO 11909) of hydrophilic polyisocyanates H) is preferably in the range from 0.3 to 20 wt %, more preferably in the range from 2 to 10 wt % and even more preferably in the range from 3 to 6 wt %.

Examples of low molecular weight aliphatic diisocyanates of component H1) are hexamethylene diisocyanate (EDI), isophorone diisocyanate (IPDI), butylene diisocyanate (BDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, of which hexamethylene diisocyanate, isophorone diisocyanate, butylene diisocyanate and bis(isocyanatocyclohexyl)methane are preferable. Hexamethylene diisocyanate, isophorone diisocyanate and butylene diisocyanate are more preferable and hexamethylene diisocyanate and isophorone diisocyanate are most preferable.

Examples of comparatively high molecular weight polyisocyanates H1) are polyisocyanates having an isocyanate functionality of 2 to 6 with isocyanurate, urethane, allophanate, biuret, iminooxadiazinetrione, oxadiazinetrione and/or uretidione groups based on the aliphatic and/or cycloaliphatic diisocyanates mentioned in the preceding section.

Preference for use as component H1) is given to comparatively high molecular weight compounds with biuret, iminooxadiazinedione, isocyanurate and/or uretidione groups based on hexamethylene diisocyanate, isophorone diisocyanate and/or 4,4'-diisocyanatodicyclohexylmethane. Isocyanurates are more preferable. Structures based on hexamethylene diisocyanate are most preferable.

Preparing polyalkylene oxides H2) by alkoxylating suitable starter molecules is literature known (e.g., Ullmanns Encyclopädie der technischen Chemie, 4th edition, volume 19, Verlag Chemie, Weinheim pp. 31-38). Suitable starter molecules are especially saturated monoalcohols such as methanol, ethanol, n-propanol, isopropanol, n-butanol, isobutanol, sec-butanol, diethylene glycol monobutyl ether and also aromatic alcohols such as phenol or monoamines such as diethylamine. Preferred starter molecules are saturated monoalcohols of the aforementioned kind. It is particularly preferable to use diethylene glycol monobutyl ether or n-butanol as starter molecules.

Monofunctional polyalkylene oxides for the purposes of the invention are compounds having just one isocyanate-reactive group, i.e., one group capable of reacting with an NCO group.

The monofunctional polyalkylene oxides H2) preferably have an OH group as isocyanate-reactive group.

The monofunctional polyalkylene oxides H2) have an OH number of 15 to 250, preferably of 28 to 112, and an ethylene oxide content of 50 to 100 mol %, preferably of 60 to 100 mol %, based on the total amount of oxyalkylene groups present.

The monofunctional polyalkylene oxides H2) typically have number-average molecular weights of 220 to 3700 g/mol, preferably of 500 to 2800 g/mol.

In a further preferred embodiment of the invention, the components A) to H) are used in the following amounts:
  A) 100 parts by weight of isocyanate-functional prepolymers,
  B) 0.01 to 5 parts by weight of alkali metal salts of weak inorganic acids,
  C) 0.1 to 200 parts by weight of water,
  D) 0 to 100 parts by weight of heterocyclic oligomers,
  E) 0 to 1 part by weight of catalysts, F) 0 to 10 parts by weight of surfactants,
G) 0 to 20 parts by weight of mono- or polyhydric alcohols, and
H) 0 to 60 parts by weight of hydrophilic polyisocyanates.

It is also advantageous when 10 to 100, preferably 20 to 90 and more preferably 20 to 80 parts by weight of heterocyclic oligomers D) are used.

The hydrophilic aliphatic polyurethane foams according to the invention can be prepared by mixing the components A), B), C) and optionally D), E), F), G) and H) in any order, foaming the mixture and curing, preferably by chemical crosslinking. The components A), D) and optionally H) are preferably premixed with each other. The components B) is preferably added to the reaction mixture in the form of their aqueous solutions.

Foaming can in principle be effected by means of the carbon dioxide formed in the course of the reaction of the isocyanate groups with water, but the use of further blowing agents is likewise possible. It is thus also possible in principle to use blowing agents from the class of the hydrocarbons such as $C_3$-$C_6$ alkanes, for example butanes, n-pentane, isopentane, cyclopentane, hexanes or the like, or halogenated hydrocarbons such as dichloromethane, dichloromonofluoromethane, chlorodifluoroethanes, 1,1-dichloro-2,2,2-trifluoroethane, 2,2-dichloro-2-fluoroethane, particularly chlorine-free hydrofluorocarbons such as difluoromethane, trifluoromethane, difluoroethane, 1,1,1,2-tetrafluoroethane, tetrafluoroethane (R 134 or R 134a), 1,1,1,3,3-pentafluoropropane (R 245 fa), 1,1,1,3,3,3-hexafluoropropane (R 256), 1,1,1,3,3-pentafluorobutane (R 365 mfc), heptafluoropropane, or else sulfur hexafluoride. Mixtures of these blowing agents can also be used.

Subsequent curing typically takes place at room temperature.

The present invention further provides compositions comprising
A) isocyanate-functional prepolymers, preferably having a weight fraction of below 1.0 wt % for low molecular weight aliphatic diisocyanates having a molar mass of 140 to 278 g/mol, based on the prepolymer, obtainable by reaction of
   A1) low molecular weight aliphatic diisocyanates having a molar mass of 140 to 278 g/mol with
   A2) di- to hexafunctional, preferably tri- to hexafunctional, polyalkylene oxides having an OH number of 22.5 to 112, preferably 31.5 to 56, and an ethylene oxide content of 50 to 100 mol %, preferably of 60 to 85 mol %, based on the total amount of oxyalkylene groups present,
B) alkali metal salts of weak inorganic acids,
C) water,
D) optionally heterocyclic 4-ring or 6-ring oligomers of low molecular weight aliphatic diisocyanates having a molar mass of 140 to 278 g/mol,
E) optionally catalysts,
F) optionally surfactants,
G) optionally mono- or polyhydric alcohols, and
H) optionally hydrophilic polyisocyanates obtainable by reaction of
   H1) low molecular weight aliphatic diisocyanates having a molar mass of 140 to 278 g/ml and/or polyisocyanates obtainable therefrom with an isocyanate functionality of 2 to 6, with
   H2) monofunctional polyalkylene oxides having an OH number of 10 to 250 and an ethylene oxide content of 50 to 100 mol %, based on the total amount of oxyalkylene groups present, wherein the alkali metal salts of weak inorganic acids B) are compounds whose corresponding free acids have a pKA value of ≥4.0 in water at 25° C.

The compositions of the present invention are particularly suitable for use in a process for producing polyurethane foams.

In a preferred embodiment of compositions according to the present invention, the alkali metal salts of weak inorganic acids B) are compounds whose corresponding free acids have a pKA value of ≥4.0 and ≤14 in water at 25° C.

The alkali metal salts of weak inorganic acids B) may more preferably be selected from the group sodium hydroxide, sodium bicarbonate and sodium carbonate.

Preference is further also given to compositions wherein the components A) to H) are present in the following amounts:
A) 100 parts by weight of isocyanate-functional prepolymers,
B) 0.01 to 5 parts by weight of alkali metal salts of weak inorganic acids,
C) 0.1 to 200 parts by weight of water,
D) 0 to 100 parts by weight of heterocyclic oligomers,
E) 0 to 1 part by weight of catalysts,
F) 0 to 10 parts by weight of surfactants,
G) 0 to 20 parts by weight of mono- or polyhydric alcohols, and
H) 0 to 60 parts by weight of hydrophilic polyisocyanates.

The compositions contain advantageously from 1 to 100, preferably from 5 to 90 and more preferably from 10 to 80 parts by weight of heterocyclic oligomers D).

The present invention further provides the polyurethane foams obtainable by the process of the present invention and also for their use as flexible foam, primary wound dressing, cosmetic article or incontinence product or use as part of one of the aforementioned products.

The invention more particularly also relates to the polyurethane foams of the present invention for use in the manufacture of primary wound dressing for treating wounds.

The invention likewise relates to polyurethane foams of the present invention as wound treatment means.

After production, the polyurethane foams can be made into sheetlike materials in a conventional manner and then can be used, for example, as a constituent of a primary wound dressing, of a cosmetic article or of an incontinence product. Generally, to this end, slab foams are cut to the desired thickness by common methods by means of which sheetlike materials having a thickness of typically from 10 μm to 5 cm, preferably from 0.1 mm to 1 cm, more preferably from 0.1 mm to 6 mm and most preferably from 0.2 mm to 6 mm, are to be obtained.

However, the sheetlike materials described can also be obtained directly using suitable casting techniques, by application and foaming of the composition according to the invention onto a substrate, for example an optionally pretreated paper or textile.

The polyurethane foams may moreover be adhered to or laminated or coated with further materials, for example materials based on hydrogels, (semi)permeable films, foam films, coatings, hydrocolloids or other foams.

The polyurethane foams according to the invention are particularly useful in the manufacture of primary wound dressings. In these dressings, the polyurethane foams can be in direct or indirect contact with the wound. Preferably, however, the polyurethane foams are used in direct contact with the wound in order that optimum absorbance of wound fluid may be ensured for example. The polyurethane foams exhibit no cytotoxicity (determined according to ISO 10993-5 and ISO 10993-12).

The polyurethane foams which are used as primary wound dressing can be additionally sterilized in a further operation. The sterilization is effected using processes known per se to one skilled in the art, wherein sterilization is effected by thermal treatment, chemical substances such as ethylene oxide or irradiation, for example by gamma irradiation. Irradiation here may be carried out under protective gas atmosphere, where appropriate. The polyurethane foams according to the invention here have the immense advantage of not discoloring on irradiation, in particular on irradiation with gamma rays.

It is likewise possible to add, incorporate or coat antimicrobially or biologically active components which have a positive effect for example in relation to wound healing and the avoidance of germ loads.

EXAMPLES

The invention we now be more particularly elucidated with reference to examples.
Substances and Abbreviations Used:
Desmodur® N 3400: Aliphatic polyisocyanate (HDI-uretidione), NCO content 21.8%, Bayer MaterialScience AG, Leverkusen, Germany
Desmodur® N 3300: Aliphatic polyisocyanate (HDI-isocyanurate), NCO content 21.8%, Bayer MaterialScience AG, Leverkusen, Germany
Polyether LB 25: Monofunctional polyether based on ethylene oxide-propylene oxide, number-average molecular weight 2250 g/mol, OH number 25 mg KOH/g, Bayer MaterialScience AG, Leverkusen, Germany
Methods:
Unless otherwise stated, percentages are all by weight.
Solids contents were determined to DIN-EN ISO 3251.
Viscosities were determined at 23° C. to DIN 53019.
NCO contents were determined volumetrically as described in DIN-EN ISO 11909.

Example 1

Preparation of Polyurethane Prepolymer 1
(Component A)

A mixture of 1000 g HDI and 1 g of benzoyl chloride was admixed at 80° C. during 3 h with 1000 g of a polyalkylene oxide having a molar mass of 4680 g/mol started on glycerol, an ethylene oxide weight fraction of 72% and a propylene oxide weight fraction of 28% and dried beforehand at 100° C. during 6 h at a pressure of 0.1 mbar, by dropwise addition and subsequently stirred for 12 h. Excess HDI was removed by thin film distillation at 130° C. and 0.1 mbar, and the non-volatile constituents were stabilized with 1 g of chloropropionic acid. This gave a prepolymer A) having an NCO content of 2.77% and a viscosity of 3500 mPas.

Example 2

Preparing a Hydrophilic Polyisocyanate
(Component H)

A mixture of 282.5 g of Desmodur N 3300 and 843.8 g of a hydroxyl-monofunctional polyether based on ethylene oxide/propylene oxide (having an ethylene oxide content of 80 mol based on the total amount of oxyalkylene groups present, number-average molecular weight 2250 g/mol and an OH number of 25 mg KOH/g was stirred in a glass apparatus at 80° C. until the titrimetrically determined NCO group content was constant. This gave a liquid having an NCO content of 4.04% and a viscosity of 3330 mPas.
Production of Foamed Materials Type and amount of prepared and foamed compositions are shown in Table 1 and FIGS. 1 and 2. The compositions were prepared as follows: The prepolymer of Example 1, the hydrophilic polyisocyanates of Example 2 and the oligomer Desmodur N3400 were filled into a vessel and homogenized therein for 15 seconds by stirring at a speed of 1200 rpm. Then, water containing the particular amount, already dissolved therein, of alkali metal salts of weak acids (amounts as per FIGS. 1 and 2) was added, followed by stirring for a further 10 seconds. The compositions thus obtained were then left to stand until a stable foam had formed as a result of the components reacting.

Cream time and gel time were determined during foaming. Cream time was the time at which the start of the reaction of the components was observable from the production of first bubbles of gas. Gel time is a time at which the composition starts to become ropy. This was tested for by repeatedly contacting the composition briefly with a plastics pipette which was then withdrawn. As soon as thread formation stopped occurring between the composition and the plastics pipette, gel time was reached.

TABLE 1

Figure 2:
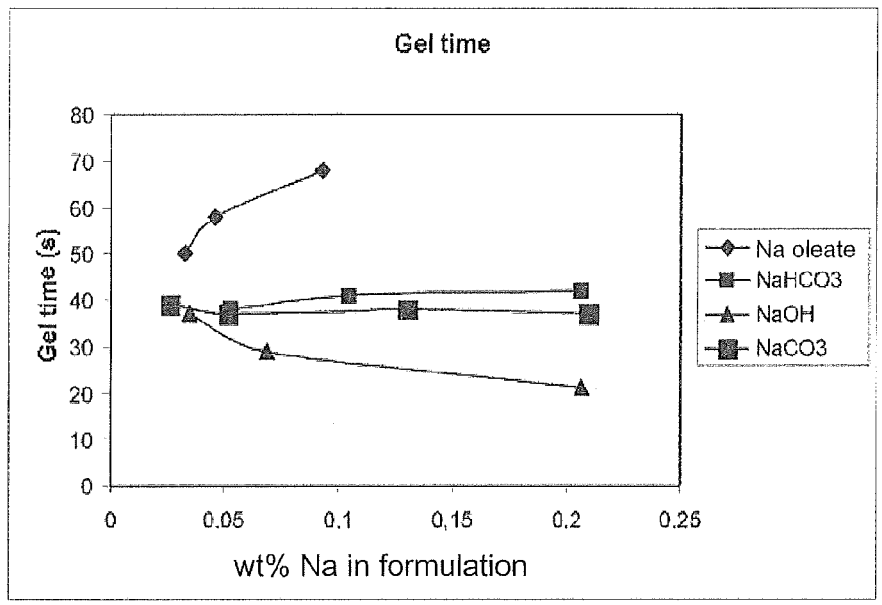
FIG. 2 shows gel time for alkali metal salts as function of sodium concentration in the formulation.

| Component | Parts by weight |
| --- | --- |
| Prepolymer A) of Example 1 | 180 |
| Oligomer D) | 25 |
| Hydrophilic PIC H) of Example 2 | 45 |
| Aqueous phase: | 34 |
| Component B) as per the amounts depicted in FIGS. 1 and 2, each supplemented with the appropriate water | |

FIGS. 1 and 2 respectively depict cream time and gel time for different alkali metal salts of weak acids as a function of the sodium concentration in the formulation and of the type of sodium salt.

In addition to the inventive polyurethane foams, which each contained an alkali metal salt of a weak inorganic acid ($NaHCO_3$, NaOH and $Na_2CO_3$), foams were also produced, as a counter-example, by using an alkali metal salt of a weak organic acid (sodium oleate).

It was found in the foaming process that the inventive compositions comprising $NaHCO_3$, NaOH or $Na_2CO_3$ had distinctly shorter cream and gel times and hence shorter reaction times than the comparative compositions comprising sodium oleate. On the other hand, the foams produced from the inventive compositions did not differ either in their chemical or in their physical properties from the foams obtained from the comparative compositions. For instance, the inventive polyurethane foams have high absorbance in respect of physiological saline or wound fluid and include only a low fraction of extractable constituents. The foams are also very highly cell-compatible.

The invention claimed is:
1. A process for producing a hydrophilic aliphatic polyurethane foam, which comprises providing a composition comprising
A) isocyanate-functional prepolymers obtained by reaction of

A1) low molecular weight aliphatic diisocyanates having a molar mass of 140 to 278 g/mol with
A2) di- to hexafunctional polyalkylene oxides having an OH number of 22.5 to 112 mg KOH/g and an ethylene oxide content of 50 to 100 mol %, based on the total amount of oxyalkylene groups present,
B) alkali metal salts of weak inorganic acids, wherein the alkali metal salts of weak inorganic acids B) are selected from the group consisting of potassium hydroxide, potassium carbonate, sodium hydroxide, sodium bicarbonate, sodium carbonate, and mixtures thereof,
C) water,
D) heterocyclic 4-ring or 6-ring oligomers of low molecular weight aliphatic diisocyanates having a molar mass of 140 to 278 g/mol,
E) optionally catalysts different from B),
F) optionally surfactants,
G) optionally mono- or polyhydric alcohols, and
H) hydrophilic polyisocyanates obtained by reaction of
H1) low molecular weight aliphatic diisocyanates having a molar mass of 140 to 278 g/ml and/or polyisocyanates obtained therefrom with an isocyanate functionality of 2 to 6, with
H2) monofunctional polyalkylene oxides having an OH number of 10 to 250 and an ethylene oxide content of 50 to 100 mol %, based on the total amount of oxyalkylene groups present,
foaming and curing the composition.

2. The process as claimed in claim 1, wherein the alkali metal salts of weak inorganic acids B) are selected from the group consisting of sodium hydroxide, sodium bicarbonate and sodium carbonate.

3. The process as claimed in claim 1, wherein isocyanate-functional prepolymers A) having a weight fraction of below 1.0 wt % for low molecular weight aliphatic diisocyanates having a molar mass of 140 to 278 g/mol, based on the prepolymer, are used.

4. The process as claimed in claim 1, wherein the components A) to H) are used in the following amounts:
A) 100 parts by weight of isocyanate-functional prepolymers,
B) 0.01 to 5 parts by weight of alkali metal salts of weak inorganic acids,
C) 0.1 to 200 parts by weight of water,
D) up to 100 parts by weight of heterocyclic oligomers,
E) 0 to 1 part by weight of catalysts,
F) 0 to 10 parts by weight of surfactants,
G) 0 to 20 parts by weight of mono- or polyhydric alcohols, and
H) up to 60 parts by weight of hydrophilic polyisocyanates.

5. The process as claimed in claim 4, wherein the composition comprises 10 to 100 parts by weight of heterocyclic oligomers D).

6. The process as claimed in claim 4, wherein the composition comprises 20 to 90 parts by weight of heterocyclic oligomers D).

7. The process as claimed in claim 4, wherein the composition comprises 20 to 80 parts by weight of heterocyclic oligomers D).

8. The process as claimed in claim 1, wherein the low molecular weight aliphatic diisocyanates A1) are hexamethylene diisocyanate (HDI), isophorone diisocyanate (IPDI) or mixtures thereof.

9. The process as claimed in claim 1, wherein the polyalkylene oxides A2) are copolymers of ethylene oxide and propylene oxide having an ethylene oxide content, based on the total amount of oxyalkylene groups present, of 60 to 85 mol %, and started on polyols or amines.

10. The process as claimed in claim 1, wherein the polyalkylene oxides A2) have number-average molecular weights of 3000 to 8500 g/mol.

11. The process as claimed in claim 1, wherein the polyalkylene oxides A2) have OH functionalities of 3 to 4.

12. The process as claimed in claim 1, wherein no catalysts E) are used.

13. A composition comprising
A) isocyanate-functional prepolymers, having a weight fraction of below 1.0 wt % for low molecular weight aliphatic diisocyanates having a molar mass of 140 to 278 g/mol, based on the prepolymer, obtained by reaction of
A1) low molecular weight aliphatic diisocyanates having a molar mass of 140 to 278 g/mol with
A2) di- to hexafunctional polyalkylene oxides having an OH number of 22.5 to 112, and an ethylene oxide content of 50 to 100 mol %, based on the total amount of oxyalkylene groups present,
B) alkali metal salts of weak inorganic acids, wherein the alkali metal salts of weak inorganic acids B) are selected from the group consisting of potassium hydroxide, potassium carbonate, sodium hydroxide, sodium bicarbonate, sodium carbonate, and mixtures thereof,
C) water,
D) heterocyclic 4-ring or 6-ring oligomers of low molecular weight aliphatic diisocyanates having a molar mass of 140 to 278 g/mol,
E) optionally catalysts different from B),
F) optionally surfactants,
G) optionally mono- or polyhydric alcohols, and
H) hydrophilic polyisocyanates obtained by reaction of
H1) low molecular weight aliphatic diisocyanates having a molar mass of 140 to 278 g/ml and/or polyisocyanates obtained therefrom with an isocyanate functionality of 2 to 6, with
H2) monofunctional polyalkylene oxides having an OH number of 10 to 250 and an ethylene oxide content of 50 to 100 mol %, based on the total amount of oxyalkylene groups present.

14. The composition as claimed in claim 13, wherein component A2) are tri- to hexafunctional polyalkylene oxides having an OH number of 31.5 to 56, and an ethylene oxide content of 60 to 85 mol %, based on the total amount of oxyalkylene groups present.

15. The composition as claimed in claim 13, wherein the alkali metal salts of weak inorganic acids B) are selected from the group consisting of sodium hydroxide, sodium bicarbonate and sodium carbonate.

16. The composition as claimed in claim 13 wherein the components A) to H) are present in the composition in the following amounts:
A) 100 parts by weight of isocyanate-functional prepolymers,
B) 0.01 to 5 parts by weight of alkali metal salts of weak inorganic acids,
C) 0.1 to 200 parts by weight of water,
D) up to 100 parts by weight of heterocyclic oligomers,
E) 0 to 1 part by weight of catalysts,
F) 0 to 10 parts by weight of surfactants,
G) 0 to 20 parts by weight of mono- or polyhydric alcohols, and H) up to 60 parts by weight of hydrophilic polyisocyanates.

17. A polyurethane foam obtained by the process as claimed in claim 1.

18. A primary wound dressing, a cosmetic article or an incontinence product comprising the polyurethane foam as claimed in claim 17.

* * * * *